United States Patent [19]
Collier et al.

[11] Patent Number: 5,917,017
[45] Date of Patent: Jun. 29, 1999

[54] DIPHTHERIA TOXIN VACCINES BEARING A MUTATED R DOMAIN

[75] Inventors: R. John Collier, Wellesley Hills; Wei Hai Shen, Boston, both of Mass.; David Eisenberg, Los Angeles; Seunghyon Choe, Solana Beach, both of Calif.

[73] Assignees: President and Fellows of Harvard College, Cambridge, Mass.; The Regents of the University of California, Oakland, Calif.

[21] Appl. No.: 08/257,781

[22] Filed: Jun. 8, 1994

[51] Int. Cl.$^6$ .......................... C07K 1/00; A61K 39/00; A61K 39/08; C12P 21/04

[52] U.S. Cl. ............... 530/350; 424/183.1; 424/184.1; 424/185.1; 424/203.1; 424/236.1; 424/245.1; 424/239.1; 435/69.1; 435/69.7; 435/29

[58] Field of Search .......................... 424/203.1, 183.1, 424/184.1, 185.1, 236.1, 245.1, 239.1; 530/350; 435/69.1, 69.7, 29

[56] References Cited

U.S. PATENT DOCUMENTS

| | | | |
|---|---|---|---|
| 4,709,017 | 11/1987 | Collier et al. ............................ | 530/350 |
| 5,601,827 | 2/1997 | Collier et al. . | |
| 5,733,726 | 3/1998 | Fu et al. . | |

OTHER PUBLICATIONS

Aron, R., "Synthetic Vaccines" published 1987 by CRC Press (FL), pp. 40–71.
Haughten et al. 1986. Vaccines 86. New Approaches to Immunization. pp. 21–25. Fred Brown et al eds.
Davis et al (ed.) 1980. Immunology. pp. 291–295.
Rolf et al. 1991. ASM. Annual Mtg. Abstract Gen. Mtg. ASM. 91:75 Abs. # B–296.
Greenfield et al. 1987. Mutations in Diphtheria Toxin Separate . . . Science 238:536–539.
Killeen et al. 1992. Reversion of recombinant toxoids: Mutations in diphtheria toxin . . . PNAS 89:6207–6209.
Rolf et al. 1990. Localization of the diphtheria toxin receptor–binding . . . JBC. 265(13):7331–7337.
Fu et al. 1993. Receptor–binding domain of diphtheria toxin as a potential immunogen. Vaccines 93, pp. 379–383.
Bixler et al. 1987. B Cell Recognition of Protein Antigens . . . In:Synthetic Vaccines (ed. Arnon). vol. 1 pp. 39–71.
Anderson, "Antibody Responses to *Haemophilus Influenzae* Type B and Diphtheria Toxin Induced by Conjugates of Oligosaccharides of the Type b Capsule with the . . . ," Infection and Immunity 39:233–238, 1983.
Anderson et al., "Immunogens Consisting of Oligosaccharides from the Capsule of *Haemophilus influenzae* Type b Coupled to Diphtheria Toxoid or the Toxin Protein CRM197," J Clin Invest 76:52–59, 1985.
Anderson et al., "Effect of Oligosaccharide Chain Length, Exposed Terminal Group, and Hapten Loading on the Antibody Response of Human Adults and Infants to Vaccines . . . ," J of Immunology 142:2464–2468, 1989.
Arnon, "Synthetic Peptides as the Basis for Future Vaccines," Trends Biochem. 11:521–524, 1986.
Baseman et al., "Action of Diphtheria Toxin in the Guinea Pig," J. Exp. Med. 132:1138–1152, 1970.
Boquet et al., "Studies on the Role of a Nucleoside–Phosphate–Binding Site of Diphtheria Toxin in the Binding of Toxin to Vero Cells or Liposomes," Eur. J. Biochem. 121:93–98, 1981.
Choe et al., "The Crystal structure of Diphtheria Toxin," Nature 357:216–222, 1992.
Eskola et al., "Antibody Levels Achieved in Infants by Course of *Haemophilus Influenzae* Type B Polysaccharide/ Diphtheria Toxoid Conjugate Vaccine," Lancelet 1:1184–1186, 1985.
Giannini et al., "The Amino Acid Sequence of Two Non–Toxic Mutants of Diphtheria Toxin: CRM45 and CRM197," Nucleic Acids Research 12:4063–4069, 1984.
Greenfield et al., "Nucleotide Sequence of the Structural Gene for Diphtheria Toxin Carried by Corynebacteriophage B," Proc. Natl Acad Sci USA 80:6853–6857, 1983.
McGill et al., "Membrane Interactions of Diphtheria Toxin Analyzed using in vitro Synthesized Mutants," The EMBO Journal 8:2843–2848, 1989.
Rolf et al., "Further Characterization of the Diphtheria Toxin Receptor–Binding Domain within HA6DT," 1991, 75th Annual Mtg FASEB J. 5:A821, #2619.
Rolf et al., "Structure–Function Analyses of Diphtheria Toxin by Use of Monoclonal Antibodies," Infection & Immunity 61:994–1003, 1993.
Tang et al., "Genetic Immunization is a Simple Method for Eliciting an Immune Response," Nature 356:152–154 1992.
Uchida et al., "Mutation in the Structural Gene for Diphtheria Toxin Carried by Temperate Phage 6," Nature New Biology 233:8–11, 1971.
Wen et al., "Diphtheria Toxin–Related α–Melanocyte–Stimulating Hormone Fusion Toxin," J. Biol. Chem. 266: 12289–12293, 1991.
Zucker et al., "Monoclonal Antibody Analysis of Diphtheria Toxin–I. Localization of Epitopes and Neutralization of Cytotoxicity," Molecular Immunology 21:785–793, 1984.
Zucker et al., "Monoclonal Antibody Analysis of Diphtheria Toxin–II. Inhibition of ADP–Ribosyl–Transferase Activity," Molecular Immunology 21:795–800, 1984.

*Primary Examiner*—Nita Minnifield
*Attorney, Agent, or Firm*—Fish & Richardson P.C.

[57] ABSTRACT

Diphtheria toxin polypeptides comprising a mutant R binding domain exhibit reduced target cell binding and may be used as vaccines to immunize a mammal against infection by *Corynebacterium diphtheria*.

27 Claims, 1 Drawing Sheet

DIPHTHERIA TOXIN VACCINES BEARING A MUTATED R DOMAIN

This invention was supported by NIH Grant Nos. AI22021 and AI22848 and the government has certain rights to this invention.

BACKGROUND OF THE INVENTION

This invention relates to vaccines which protect against diphtheria toxin.

Wild-type diphtheria toxin (DT) is a protein exotoxin produced by the bacterium *Corynebacteria diphtheria*. The molecule is produced as a single polypeptide that is proteolytically cleaved at amino acid residue 190, 192, or 193 into two subunits linked by a disulfide bond: fragment A (N-terminal ~21K) and fragment B (C-terminal ~37K) (Moskaug, et al., *Biol Chem* 264:15709–15713, 1989; Collier et al., *Biol Chem*, 246:1496–1503, 1971). The receptor binding domain of wild-type DT is contained within the B fragment (Rolfe et al., *J. Biol. Chem.*, 265:7331–7337, 1990). Fragment A is the catalytically active portion of wild-type DT. It is an NAD-dependent ADP-ribosyltransferase which inactivates protein synthesis factor elongation factor 2 (EF-2), thereby shutting down protein synthesis in the intoxicated cell. Fragment B of wild-type DT possesses the receptor-binding domain known as the R domain (amino acids 379–535, see Choe et al., *Nature*, 357:216–222, 1992; Fu et al., In Vaccines 93, Ginsberg et al., Eds., CSHSQB, pp. 379–383, 1993). The receptor-binding domain comprises 10 β strands which form two βsheets. A subset of the βstrands resembles an immunoglobulin-like moiety, which is conceivably involved in receptor recognition (Choe et al., *Nature* 357:216–222, 1992). Once DT is bound to the cell via the receptor binding domain, the receptor/DT complex is internalized. A second functional region on fragment B acts to translocate DT across the cell membrane, releasing catalytically active fragment A into the cytosol of the cell. A single molecule of fragment A is sufficient to inactivate cellular protein synthesis.

Immunity to a bacterial toxin such as wild-type DT may be acquired naturally during the course of infection, or artificially by injection of a detoxified form of the toxin (also called a chemical toxoid) (Germanier, ed., *Bacterial Vaccines*, Academic Press, Orlando, Fla., 1984). Chemical toxoids have traditionally been prepared by chemical modification of native toxins (e.g., with formalin or formaldehyde (Lingood et al., *Brit. J. Exp. Path.* 44:177, 1963), rendering them non-toxic while retaining antigenicity that protects the vaccinated animal. An example of a chemical toxoid is that described by Michel and Dirkx (*Biochem. Biophys. Acta* 491:286–295, 1977). However, a chemical toxoid may lose the added chemical group or groups, and revert to its active, toxic form, so that its use as a vaccine poses a risk to the vaccinee.

Another avenue for producing a toxoid is by the use of genetic techniques. A *Corynebacterium diphtheriae* mutant, CRM-197 (Uchida et al., *J. Biol. Chem.* 248:3838–3844, 1973; Uchida, et al., *Nature* 233:8–11, 1971) (CRM standing for "cross-reacting material") was shown to contain an enzymatically inactive DT protein which produces an anti-DT immune response. Collier et al. (U.S. Pat. No. 4,709,017; herein incorporated by reference) discloses a genetically engineered DT mutant that bears an amino acid deletion at Glu-148. Substitution of Asp, Gln or Ser at this site diminishes enzymatic and cytotoxic activities by 2–3 orders of magnitude, showing that the spatial location and chemical nature of the Glu-148 side chain greatly affects these activities (Carroll et al., *J. Biol. Chem.* 262:8707, 1987; Tweten et al., *J. Biol. Chem.* 260:10392, 1985; Douglas et al., *J. Bacteriol.* 169:4967, 1987).

Similarly, Greenfield et al. (U.S. Pat. No. 4,950,740; herein incorporated by reference) discloses genetically engineered mutant forms of DT in which the Glu 148 residue is deleted or replaced with Asn. The DNA sequence and corresponding amino acid sequence of naturally occurring diphtheria toxin DNA is set forth in FIG. 1 (SEQ ID NO:1).

SUMMARY OF THE INVENTION

The invention features polypeptides comprising a mutant diphtheria toxin (toxoid) R domain that can be used as a vaccine against the toxic effects of wild-type (i.e., naturally occurring) DT. The mutant R domain consists of an amino acid segment between amino acids 379–535, inclusive, of SEQ ID NO: 1, which is mutated in at least one amino acid position so as to reduce but not eliminate target cell receptor binding. It is preferable to retain other functional domains in addition to the R domain in such vaccines in order to maximize protein stability and optimize epitope diversity. On the other hand, a vaccine or live vaccine strain comprising a single domain such as the R domain is less likely to revert to toxicity. The invention also features live, genetically engineered microorganisms (cells and viruses) expressing a polypeptide comprising a mutant DT R domain. A toxoid of the invention comprises a mutant R domain that binds target cells with less efficiency than wild-type DT. A toxoid of the invention, and the DNA encoding a toxoid of the invention carry less risk of reversion and are better candidates for use in a live, genetically engineered vaccine cell or virus, each of which is capable of proliferating in the vaccinee. Preferably, the toxoids include a mutant R domain that is immunologically cross-reactive with naturally occurring diphtheria toxin—i.e., it reacts with antibodies that are monospecific for naturally occurring diphtheria toxin.

Mutated, or mutant, as used herein, refers to a sequence change (substitution or deletion) which results in a deletion of one or more of amino acids 379–535, or substitution of at least one of those amino acids with one or more other amino acids.

Applicants have shown how to construct DT toxoids comprising a mutant R domain which are safe to administer to a patient in the form of a live vaccine strain. Use of a live vaccine strain has many advantages over immunizing with a chemical toxoid. For example, 1) a live vaccine strain proliferates in the recipient and is capable of expressing a DT toxoid; 2) a live vaccine strain remains in the vaccinee longer than would an injected polypeptide, and is capable of producing a genetically engineered DT toxoid; and 3) a live vaccine may require fewer injections or boosters for effective immunization, can often be orally administered, and can be used to administer multiple antigens at once. Alternatively, toxoids of the invention may be combined with a pharmaceutically suitable vehicle to form a vaccine composition that is inoculated into a mammal, and generates immunological protection against wild-type diphtheria toxin. A toxoid of the invention is produced by culturing a cell that includes a DNA encoding a DT toxoid and regulatory DNA capable of directing expression of the DT toxoid.

In general, the invention features a polypeptide, preferably a substantially pure preparation of a polypeptide, the polypeptide comprising a mutant diphtheria toxin R domain, preferably encoding both a mutant R domain and at least part of the B fragment, or encoding a mutant R domain and at least part of the A fragment, more preferably a mutant R domain and a B fragment and at least part of an A fragment, most preferably a mutant R domain and the B fragment and all of fragment A, in which the R domain comprises a mutation in at least one or more of Lys 516, Lys 526, Phe 530, or Lys 534 (FIG. 1; SEQ ID NO: 1), preferably the Lys 516, Lys 526, or Lys 534 is replaced by Cys or Phe, and the Phe 530 is substituted by any one of Glu, Lys, or Gln, the B fragment, above, lacking the segment between amino acids 379–535, inclusively of wild-type DT (FIG. 1; SEQ ID NO: 1). A polypeptide of the invention, as used herein, refers to a polypeptide comprising a mutant R domain as exemplified or claimed herein. As used herein, the term "substantially pure" describes a DT protein which has been separated from components which naturally accompany it. Typically, a protein is substantially pure when at least 10% of the total material (by volume, by wet or dry weight, or by mole per cent or mole fraction) is a DT protein. Preferably the protein is at least 50%, more preferably at least 75%, even more preferably at least 90%, most preferably at least 99% of the total material. Purity can be conveniently assayed by well known methods such as SDS-PAGE gel electrophoresis, column chromatography, or HPLC analysis.

In a related aspect, the invention features a cell comprising a nucleic acid encoding a polypeptide of the invention, preferably a homogeneous population of cells, preferably any one of a *B. subtilis, Bacillus Calmette-Guerin* (BCG), Salmonella sp., *Vibrio cholerae, Corynebacterium diphtheria, Listeriae,* Yersiniae, Streptococci, or *E. coli* cell. The cell is preferably capable of expressing a polypeptide of the invention.

In another aspect, the invention features a vaccine comprising a physiologically acceptable mixture including a polypeptide of the invention.

In a related aspect, the invention features a live vaccine strain comprising a cell that expresses an above-described polypeptide of the invention.

In another aspect, the invention features a method of preparing a polypeptide of the invention comprising providing a cell growing the cell in a medium to form a population of cells that express the polypeptide and obtaining the polypeptide from a population of cells or the medium.

In a related aspect, the invention also features a method for manufacturing a vaccine comprising culturing a cell comprising a polypeptide of the invention under conditions permitting proliferation of the cell, the cell being suitable for introduction into an animal as a live vaccine cell.

The invention also features a method of immunizing a mammal, preferably a human, against wild-type diphtheria toxin, the method comprising introducing an immunizing amount of a vaccine into the mammal. One, but not the only, method of administering a DNA encoding a diphtheria toxoid of the invention is by biolistic transfer, a method of delivery involving coating a microprojectile with DNA encoding an immunogen of interest, and injecting the coated microprojectile directly into cells of the recipient (Tang, et al., *Nature* 356:152–154, 1992). The diphtheria toxoid of the invention is then expressed from the DNA to stimulate an immune response in the recipient.

In another aspect, the invention features a fusion polypeptide comprising a polypeptide linked by a peptide bond to a second polypeptide. A second polypeptide, as used herein, confers stability to and/or aids or enhances the immunogenicity of a mutant R domain or a polypeptide of the invention.

A fusion polypeptide consists of a polypeptide of the invention linked by a peptide bond to a second polypeptide. Preferably, the fusion polypeptide is included in a vaccine, which can be used to immunize a human patient against wild-type diphtheria toxin. Additionally, a polypeptide of the invention can act as a carrier substance for a second polypeptide, forming a fusion polypeptide and preferably enhancing the immunogenicity of the second polypeptide. The DNA encoding the fusion polypeptide can be used directly as a vaccine, or can be incorporated into a cell, the cell (e.g. a live vaccine cell), is capable of expressing the fusion polypeptide, and, preferably, is used as a vaccine against wild-type diphtheria toxin. "Fusion polypeptide," as used herein, refers to a protein molecule produced by expression of a DNA in which the DNA encodes a polypeptide of the invention, the polypeptide linked by means of genetic engineering to a second DNA encoding a second polypeptide sequence. A "fusion polypeptide of the invention," as used herein, refers to a fusion polypeptide comprising a mutant R domain.

In another aspect, the invention features a DNA molecule comprising a sequence encoding a mutant diphtheria toxin R domain, preferably encoding both a mutant R domain and at least part of the B fragment, or encoding a mutant R domain fragment and at least part of the A fragment, more preferably a mutant R domain and a B fragment and at least part of an A fragment, most preferably a mutant R domain and the B fragment and all of fragment A, where the DNA sequence complimentary to the codon corresponding to at least one of Lys 516, Lys 526, Phe 530, or Lys 534 of naturally-occurring diphtheria toxin (FIG. 1; SEQ ID NO: 1) is mutated, preferably the Lys 516, Lys 526, or Lys 534 is substituted by either Cys or Phe, and the Phe 530 is substituted by a any one of Glu, Lys, or Gln, the B fragment, above, lacking amino acids 379–535, inclusively.

In another aspect, the invention features a DNA molecule comprising a sequence encoding a mutant diphtheria toxin R domain and at least part of the B fragment, the B fragment comprising a mutation at any one of Glu 349, Asp 352, or Ile 364 of wild-type diphtheria toxin (FIG. 1, SEQ ID NO: 1) and lacking amino acids 379–535, inclusively.

In another aspect, the invention features a DNA molecule comprising a sequence encoding a mutant diphtheria toxin R domain, the B fragment, and at least part of the A fragment, the A fragment comprising a mutation at any one of His 21, Glu 22, Lys 39, Gly 52, Gly 79, Gly 128, Ala 158, Gly 162, Glu 142, Val 147, Glu 148 of wild-type diphtheria toxin (FIG. 1, SEQ ID NO: 1), the B fragment, above, lacking amino acids 379–535, inclusively.

In another aspect, the invention features a DNA sequence encoding the polypeptide encoded by the DNA sequence shown in SEQ ID NO:2.

In another aspect, the invention features a polyclonal antibody produced by injecting a mammal with the diphtheria toxin R domain.

In another aspect, the invention features a monoclonal antibody capable of binding the diphtheria toxin R domain.

In a related aspect, the invention features a polypeptide including a mutant R domain, wherein the R domain includes at least one mutation between amino acids 379–535 of SEQ ID NO: 1, inclusive. The polypeptide binds sensitive cells with less affinity than wild-type diphtheria toxin and is capable of forming an immune complex with an antibody which specifically recognizes the R domain of wild-type diphtheria toxin. A sensitive cell, as used herein, is any cell which is killed by wild-type diphtheria toxin as determined by cytotoxicity assays described herein.

In a related aspect, the invention features a DNA molecule including a sequence encoding a mutant diphtheria toxin R domain, wherein the DNA sequence complimentary to a codon corresponding to at least one amino acid between 379–535 of SEQ ID NO: 1, inclusive, is mutated.

A "live vaccine cell," or "live vaccine strain," as used herein, is either a naturally avirulent live microorganism, or a live microorganism with either low or attenuated virulence, that expresses an immunogen.

The invention also features polypeptides that are covalently attached to a moiety, e.g., a polysaccharide or a second polypeptide. The moiety may serve as a carrier substance for a polypeptide of the invention; or, alternatively, a polypeptide of the invention can serve as a carrier substance for the moiety, preferably enhancing the immunogenicity of the moiety. Preferred polysaccharides include dextran, PrP (the capsular polysaccharide of *H. influenzae* b) and pneumococcal polysaccharides (types 14, 6B or 23F). A "carrier substance" is a substance that confers stability to, and/or aids or enhances the transport or immunogenicity of, an associated molecule.

In a related aspect, the invention features a polypeptide of the invention comprising a carrier substance which enhances the immunogenicity of a moiety or the polypeptide. Examples of preferred carrier substances have been listed above.

A polypeptide or fusion protein of the invention can be made by any suitable method, preferably by culturing any of the various cells containing a DNA encoding a diphtheria toxoid of the invention under conditions permitting the expression of the DNA.

Expression of a diphtheria toxoid of the invention is under the control of a heterologous promoter, and/or the expressed amino acids are linked to a signal sequence. Vectors comprising DNA encoding toxoids of the invention can be made by molecular techniques well known in the art (See Sambrook et al., *Molecular Cloning*, 2nd ed., (1989)). By "heterologous promoter" is meant a promoter region that is not identical to the promoter region found in a naturally occurring diphtheria toxin gene. The promoter region is a segment of DNA 5' to the transcription start site of a gene, to which RNA polymerase binds before initiating transcription of the gene.

An "essentially pure" preparation of the nucleic acid of the invention is a preparation containing the nucleic acid of the invention, and which is substantially free of other nucleic acid molecules with which a nucleic acid encoding wild-type diphtheria toxin is naturally associated in Corynebacterium.

Wild-type or naturally occurring DT, as used herein, refers to the diphtheria toxin protein found in nature as shown in SEQ ID NO: 1. Pseudo-wild-type DT, as used herein, refers to the diphtheria toxin protein comprising a Glu→Ser mutation at amino acid 148. Those skilled in the art will know that, in the laboratory, handling pseudo-wild-type DT is safer than handling wild-type DT. A mutant DT protein, as used herein, is DT protein comprising a mutant R domain as exemplified herein. Polypeptides of the invention that are "immunologically cross-reactive," as that term is used herein, possess at least one antigenic determinant in common with naturally occurring diphtheria toxin, so that they are each bound by at least one antibody with specificity for naturally occurring diphtheria toxin.

Other features and advantages of the invention will be apparent from the following detailed description and from the claims.

DETAILED DESCRIPTION

Figure 1:
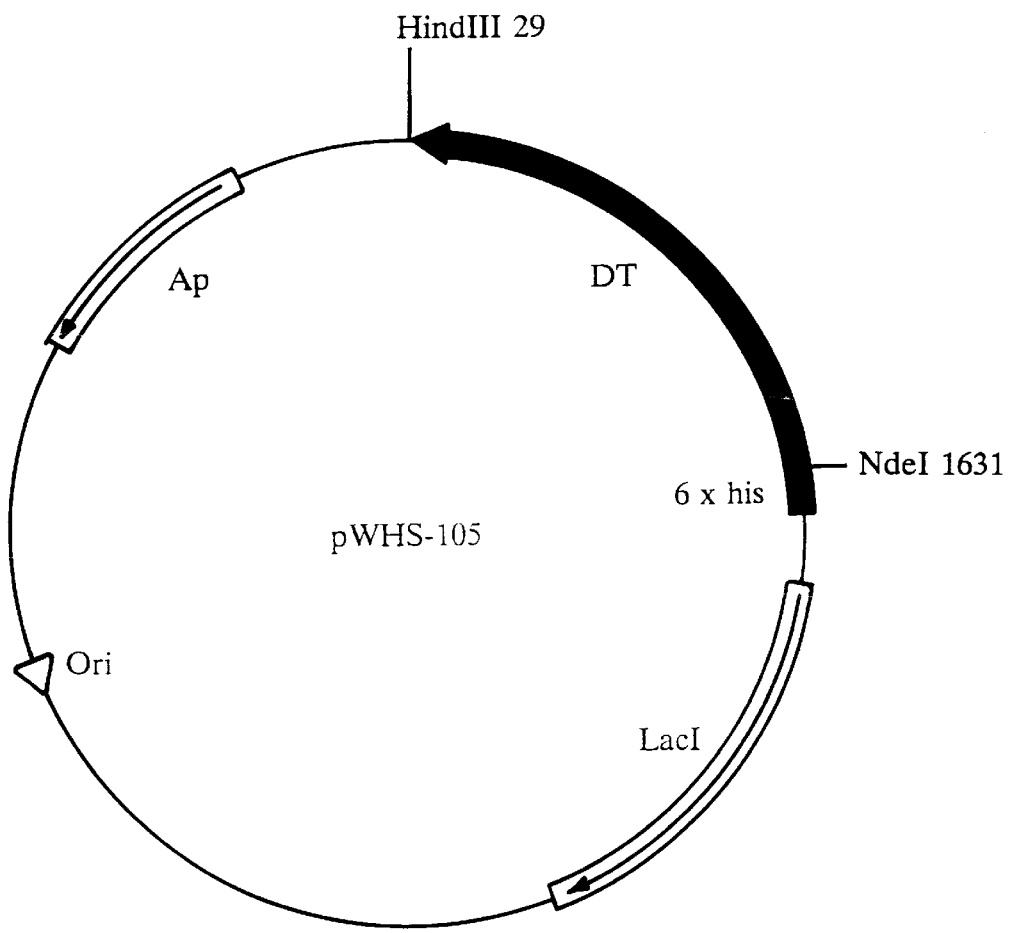

We first briefly describe the drawings.

Drawings

FIG. 1 is a drawing of the DNA vector PWHS-105 comprising the DT gene. HindIII and NdeI restriction enzyme sites are indicated. 6 X His refers to six consecutive histidine residues used to purify the DT protein.

Table I is a list of mutations in the diphtheria toxin R domain made by site directed mutagenesis.

Table II is the result of testing the cytotoxicity of wild-type DT, pseudo-wild-type DT, and various mutant DT proteins.

Methods

1. Cloning and Expression of the DT Gene

The DT gene (O'Keefe et al., *PNAS* (USA) 86: 343–346, (1989)) was PCR-amplified, then cut with NdeI and Hind III. The gene fragment has inserted into a PET-5bexpression vector (Novagen) in order to make PWHS105. By using this vector, and the manufacturer's instructions, the expressed DT protein carries six consecutive histidine residues at the N-terminal end. The modified vector comprising the DT gene was termed PWHS105 (FIG. 1). Multiple histidine residues bind the DT protein to a $Ni^{2+}$-column prepared according to the manufacturer's instructions (Novagen). After unbound proteins were washed away, the DT protein was collected by elution with imidazole. DT protein purity is above 99% with this method, and the yield is ~1–2 mg per 50 ml bacterial culture. Bacterial transformation was accomplished according to standard procedures (Sambrook et al., *Molecular Cloning*, (1989) pp. 1.74–1.105).

I. Alternative DNA Vectors

DNA encoding DT or a polypeptide of the invention may also be carried on any other vector operably linked to control signals capable of effecting expression in a prokaryotic host. If desired, the coding sequence can contain, at its 5' end, a sequence encoding any of the known signal sequences capable of effecting secretion of the expressed protein into the periplasmic space of the host cell, thereby facilitating recovery of the protein. Prokaryotes most frequently used are represented by various strains of *E. coli*; however, other microbial strains can also be used, e.g., *C. diphtheriae*. Additional plasmid vectors may be used which contain replication origins, selectable markers, and control sequences derived from a species compatible with the microbial host. For example, *E. coli* can be transformed using derivatives of PBR322, a plasmid constructed by Bolivar, et al. (1977, *Gene* 2:95) using fragments derived from three naturally-occurring plasmids, two isolated from species of Salmonella, and one isolated from *E. coli*. PBR322 contains genes for ampicillin and tetracycline resistance, and thus provides multiple selectable markers which can be either retained or destroyed in constructing the desired expression vector. Commonly used prokaryotic expression control sequences (also referred to as "regulatory elements") are defined herein to include promoters for transcription initiation, optionally with an operator, along with ribosome binding site sequences. Promoters commonly used to direct protein expression include the beta-lactamase (penicillinase), the lactose (lac) (Chang et al., 198 *Nature* 1056, 1977) and the tryptophan (trp) promoter systems (Goeddel et al., 8 *Nucl. Acids Res.* 4057, 1980) as well as the lambda-derived PL promoter and N-gene ribosome binding site (Shimatake et al., 292 *Nature* 128, 1981). Examples of microbial strains, vectors, and associated regulatory sequences are listed herein to illustrate, but not to limit, the invention.

By way of example, vectors other than PET-15b (Novagen) can be used to express the polypeptides of the invention, or a fusion protein including the polypeptides of the invention. These vectors may consist of (i) an origin of replication functional in *E. coli* derived from the plasmid PBR322 ; (ii) a selectable tetracycline resistance gene also derived from PBR322 ; (iii) a transcription termination region, e.g., the termination of the *E. coli* trp operon (placed at the end of the tetracycline resistance gene to prevent transcriptional read-through into the trp promoter region); (iv) a transcription promoter, e.g., the trp operon promoter, or the diphtheria toxin promoter; (v) the R region protein coding sequence; and (vi) a transcription terminator, e.g., the T1T2 sequence from the ribosomal RNA (rrnB) locus of *E. coli*. The sequences of carrier molecules, the methods used in the synthesis of the DNA sequences, the construction of fusion genes, and the appropriate vectors and expression systems are all well known to those skilled in the art. Similar expression systems can be designed for fusion or non-fusion polypeptides, i.e., for expression of the R region polypeptide alone. These procedures are further examples of, but are not limiting on, the methods of the invention.

II. Alternative Protein Purification and Synthesis

One schooled in the art can purify polypeptides of the invention using other conventional methods of protein isolation, e.g., methods including but not limited to precipitation, chromatography, immunoadsorption, or affinity techniques. The polypeptides can be purified from starting material using protease-treated diphtheria toxin, or using the cells, or medium of the cells, of a vaccine strain genetically engineered to express a polypeptide of the invention. Purification can also be achieved by making another fusion protein of a polypeptide with another recombinant protein, e.g., with a fragment of the maltose binding protein in a manner similar to that described above. These fusion constructs can be made, for example, with the vector PMAL (New England Biolabs) or the PGEX-3X or -2T vectors (Pharmacia), described above. Fusion proteins are purified on affinity columns specific for the maltose binding protein or the glutathione-S-transferase protein, respectively.

Polypeptides of the invention can, in some cases, also be synthesized by non-biological means, for example organic chemical synthesis, or cleaved from a larger protein containing the amino acid sequences of the invention. For example, organic chemical synthesis can be performed by conventional methods of automated peptide synthesis, or by classical organic chemical techniques. Diphtheria toxin protein or fragment B can be purified, for example, by the method of Carroll et al. (*Meth Enzymol* 165:68–76, 1988).

2. Characterization of Diphtheria Toxin Cytotoxicity

The cytotoxicity of pseudo-wild-type DT and wild-type DT was evaluated in a cytotoxicity assay (*Meth. in Enz.* 165:220–221, 1988. The data show pseudo-wild-type DT has an ID50 value of $3.8 \times 10^{-11}$ M, while the ID50 value of wild-type DT is $10^{-13}$ M. The difference in cytotoxicity between these two proteins is due to the mutation of the A fragment active site at amino acid 148 of DT. Polypeptides of the invention may be tested for cytotoxicity in this assay. Additional embodiments of the assay include adding both a polypeptide of the invention and wild-type DT to cells in order to check for the ability of a polypeptide of the invention to block the toxic activity of wild-type DT. In another embodiment of the cytotoxicity assay, it is possible to screen antibodies which bind wild-type DT or a polypeptide of the invention by combining each with an antibody under conditions which allow binding of the antibody to the polypeptide or wild-type DT and checking for cell toxicity in the cytotoxicity assay. Antibodies capable of binding wild-type DT or a polypeptide of the invention will prevent cell toxicity.

3. Site-Directed Mutagenesis of DT

To identify amino acids in the diphtheria toxin R domain involved in receptor binding and to make mutant DT proteins, we used well known DNA primer based site-directed mutagenesis (site directed mutagenesis (M13) kit from Amersham). specific DNA primers used for site directed mutagenesis are disclosed (SEQ ID NOs: 3–28). The Amersham kit was used according to the manufacturer's instructions in order to mutate specific residues within the R domain. We produced a total of twenty-four mutant DT proteins (see Table 1). Mutant DT proteins were purified by a $Ni^{2+}$-column (Novagen) according to the manufacturer's instructions.

4. Amino Acid Positions 516 and 530 Are Receptor Binding Sites

Cells which are sensitive to diphtheria toxin possess cell receptors which bind and internalize the toxin. Generally, such cells are killed when exposed to wild-type diphtheria toxin. The ability of purified mutant DT proteins to bind cells via a diphtheria toxin receptor was evaluated by cytotoxicity assay (above). The results of the cytotoxicity assay using pseudo-wild-type DT (so called "WT" in Table 2) and selected DT mutant proteins are shown in Table 2. In Table 2, a DT mutant protein is given two letters and a number as a convenient abbreviation. The first letter refers to the normal amino acid, the number is the amino acid residue in SEQ ID No: 1, and the last letter, the substituted amino acid of the mutant protein. The mutant DT protein K516A has $\frac{1}{20}$ the toxicity of DT. Given that pseudo-wild-type DT has roughly $\frac{1}{400}$ of the toxicity of wild-type DT, K516A has $\frac{1}{8000}$ the toxicity of wild-type DT. The mutant protein F530A is less toxic than DT by a factor of 9 and has $\frac{1}{3500}$ the toxicity of the wild-type DT. These data confirm that Lys 516 and Phe 530 are important for the binding of wild-type diphtheria toxin to diphtheria toxin receptors on the cells. Moreover, the conservative change from lysine to glutamic acid at amino acid 516 demonstrates that the positive charge of 516K contributes to the binding activity of wild-type diphtheria toxin.

TABLE 1

DT Mutant List

| Amino Acid | Amino Acid Mutation | Codon Mutation | Amino Acid | Amino Acid Mutation | Codon Mutation |
|---|---|---|---|---|---|
| 510 | Gly → Ser, | GGC → AGT | | | |
| 512 | Leu → Glu, | CTT → GAA | Amino Acid | Amino Acid Mutation | Codon Mutation |
| 514 | Tyr → Ala, | TAC → GCC | 514 | Tyr → Ala, | TAC → GCC |

TABLE 1-continued

DT Mutant List

| 516 | Lys → Glu, | AAA → GAA | 516 | Lys → Ala, | AAA → GCA |
| 518 | Val → Glu, | GTA → GAA | 518 | Val → Ala, | GTA → GCA |
| 520 | His → Asp, | CAC → GAC | 520 | His → Ala, | CAC → GCC |
| 521 | Thr → Arg, | ACC → CGC | 521 | Thr → Ala, | ACC → GCC |
| 522 | Lys → Glu, | AAG → GAG | 522 | Lys → Ala, | AAG → GCG |
| 523 | Val → Glu, | GTT → GAA | 523 | Val → Ala, | GTT → GCT |
| 524 | Asn → Ala, | AAT → GCT | 524 | Asn → Ala, | AAT → GCT |
| 525 | Ser → Phe, | TCT → TTT | 525 | Ser → Ala, | TCT → GCT |
| 526 | Lys → Glu, | AAG → GAG | 526 | Lys → Ala, | AAG → GCG |
| 528 | Ser → Tyr, | TCG → TAT | 528 | Ser → Ala, | TCG → GCG |
| 530 | Phe → Ser, | TTT → TCT | 530 | Phe → Ala, | TTT → GCT |

TABLE 2

| DT, M | $10^{-12}$ | $10^{-11}$ | $2 \times 10^{-11}$ | $4 \times 10^{-11}$ | $8 \times 10^{-11}$ | $10^{-10}$ | $2 \times 10^{-10}$ | $4 \times 10^{-10}$ | $8 \times 10^{-10}$ | $10^{-9}$ | $10^{-8}$ | ID50 $10^{-11}$ | ID50 relv. |
|---|---|---|---|---|---|---|---|---|---|---|---|---|---|
| WT | .953 | .805 | .728 | .47 | .247 | .169 | .085 | .04 | .028 | .023 | .018 | 3.77 | 1 |
| Y514A | 1.01 | 1.06 | 1.01 | .983 | .832 | .706 | .452 | .288 | .193 | .190 | .142 | 12.2 | 3 |
| K516A | .846 | .869 | .805 | .875 | .821 | .900 | .797 | .674 | .508 | .438 | .057 | 82.3 | 20 |
| V518A | .905 | .925 | .821 | .739 | .522 | .448 | .253 | .118 | .067 | .058 | .037 | 8.6 | 2 |
| H520A | .979 | .916 | .677 | .477 | .256 | .215 | .097 | .047 | .036 | .037 | .026 | 3.8 | 1 |
| T521A | .947 | .840 | .744 | .518 | .254 | .197 | .093 | .050 | .036 | .030 | .023 | 4.3 | 1 |
| K522A | .952 | .902 | .781 | .575 | .337 | .257 | .125 | .047 | .028 | .022 | .014 | 5.3 | 1 |
| V523A | 1.02 | 1.01 | .975 | .929 | .814 | .724 | .51 | .312 | .154 | .128 | .058 | 21.0 | 5 |
| N524A | .904 | .89 | .89 | .771 | .607 | .552 | .34 | .155 | .074 | .067 | .020 | 12.5 | 3 |
| S525F | 1.02 | .978 | .937 | .957 | .80 | .744 | .566 | .325 | .177 | .134 | .043 | 25.5 | 6 |
| S525A | .897 | .767 | .654 | .524 | .263 | .205 | .089 | .035 | .022 | .021 | .016 | 4.4 | 1 |
| K526A | .95 | .905 | .883 | .856 | .72 | .72 | .46 | .455 | .14 | .092 | .029 | 23.0 | 6 |
| S528A | .942 | .935 | .865 | .704 | .457 | .373 | .193 | .069 | .043 | .039 | .030 | 7.3 | 2 |
| F530A | .873 | .82 | .835 | .858 | .851 | .783 | .649 | .37 | .211 | .178 | .065 | 30.7 | 9 |

5. Binding Competition between $^{125}$I-Labelled Wild-Type DT and Mutant DT Proteins Wild-type and mutant DT proteins were labelled with $^{125}$I by standard methods (see Bolton-Hunter, *Biochem J.*, 133:529, 1973) to further demonstrate that amino acids at positions 516 and 530 are involved in receptor binding. At 4° C. the affinity of both DT mutant proteins K516A and K516E are 1/500 of DT, and the affinity of both DT mutant proteins F530A and F530S are 1/100 that of DT.

6. Preparation of Antisera Against the R Domain of Wild-Type DT

The purified receptor binding domain of wild-type DT (See Choe et al., supra) was used as antigen to produce polyclonal antibody. The immunogenicity of the receptor binding domain protein was tested in two white New Zealand female rabbits. 1 ml of 350 μg of DTR in Tris buffer, PH 8.0, was mixed with 1 ml of complete Freund's adjuvant for the first dose and incomplete Freund's adjuvant for subsequent doses. Immunizations were given at 0, 20, 40, and 60 days. Serum samples were taken at 30, 50, and 70 days. Antisera were able to recognize not only the receptor binding domain, but also wild-type DT in standard Western blotting experiments (see Harlow and Lane in *Antibodies, a Laboratory Manual*, (1988)). Specific reactivity was observed after the first boost at 12,800-fold dilution and increased after the second and third boost in ELISA assays (See Harlow and Lane, supra).

A 10-fold dilution of the antisera was tested for ability to neutralize the toxic effect of wild-type DT on Vero cells. Briefly, wild-type DT ($10^{-12}$M) was incubated with various concentrations of antisera for 1 hr at 37° C. with Vero cells. Cytotoxicity was evaluated as previously described (Carrol and Collier, supra). After the third boost, the antisera was able to neutralize up to 72% of the toxicity of wild-type DT.

The ability to efficiently raise antibodies against the receptor binding domain, as demonstrated herein, suggests that the use of a polypeptide comprising a mutant R-domain or the mutant R domain alone could provide an effective vaccine with less or no toxicity. Having demonstrated that polyclonal antisera against the receptor binding domain of wild-type DT is readily obtained, those skilled in the art would know that a monoclonal antibody could also be obtained by following standard immunological methods (see Harlow and Lane, supra). The immunogenicity of the receptor binding fragment indicates that a polypeptide comprising a mutant R domain is also immunogenic and prophylactic against exposure to wild-type DT. Polyclonal or monoclonal antibodies against the receptor binding domain of wild-type DT can be used to test whether a polypeptide of the invention is antigenic (see below).

I. Western Blotting 0.5 μg of wild-type DT was loaded onto a divided 12% polyacrylamide minigel. After electrophoresis, the protein was transferred to a nitrocellulose membrane. The membrane bearing transferred protein was cut into pieces and incubated with various dilutions of antisera, separately. The sectioned membranes were then incubated with first antibody, Diphtheria Antitoxin USP (Connaught Laboratories, Inc.), followed by second antibody, anti-horse IgG alkaline phosphatase conjugate (Sigma) and developed with Tris buffer, Ph 9.6, containing 0.01% of nitroblue tetrazolium and 0.01% of 5-bromo-4-chloro-3-indolyphosphate (Sigma).

7. Evaluation of Antigenicity

It is possible to conveniently test whether a polypeptide of the invention is antigenic and likely to serve as an effective vaccine by exhibiting desirable antigenic properties. Standard diphtheria antitoxin and polyclonal antisera against the purified receptor binding domain of wild type DT can be used to establish the antigenicity of polypeptides of the invention.

(i) Total Antigenic Activity (Lf): The antigenic activity of each purified polypeptide of the invention in terms of flocculating units (Lf) can be measured by the standard flocculation reaction against standard diphtheria antitoxin from the Center for Biologics Evaluation and Research, FDA, Bethesda, MD. The test will be performed by the method of Ramon Relyreld, E. M. (1969) Prog. in Immun. Stand. 3, 258–263. Activity will be expressed in Lf/mg protein.

(ii) Evaluation of Antigenicity with Polyclonal Antisera: Polyclonal antisera against the purified receptor binding domain of wild-type DT can be used to bind polypeptides of the invention. The preservation of antigenic epitopes of wild-type DT in polypeptides of the invention will be evaluated quantitatively in two systems, the classical quantitative precipitin reaction (above) and by competitive ELISA (see Harlow and Lane, supra).

(iii) Ouantitative Precipitin Reaction: This method has the advantage of allowing antibodies (e.g., standard diphtheria antitoxin or polyclonal sera against purified DT receptor binding domain) to bind polypeptides in the fluid phase, avoiding the potentially distorting effects that can be observed when proteins are bound to nitrocellulose. In addition, it provides precise quantitative information of the amount of antibody precipitable by each polypeptide of the invention. The maximal precipitable antibody will be quantitated using the method of Pappenheimer et al. (*Immunochemistry* 9, 891–906 (1992). Purified wild-type diphtheria toxin, formalinized diphtheria toxin (i.e. chemical toxoid) and a polypeptide of the invention will be used as controls. These controls can be used to precipitate diphtheria toxin directed antibodies. The total antibody protein precipitable by each polypeptide will be expressed as a proportion of the antibody precipitable by the control toxins or toxoids and will serve as a measure of how well all diphtheria antigenic epitopes have been preserved in the polypeptides of the invention.

The supernatants of the quantitative precipitin reactions will be evaluated for their remaining antitoxin activity at their point of equivalence (point where maximal toxin protein and antibody are precipitated). The control toxin proteins are expected to precipitate all neutralizing activity. The completeness of the precipitation of neutralizing activity by polypeptides of the invention will provide a quantitative measure of how well neutralizing epitopes have been preserved in the mutant polypeptides of the invention.

(iv) Competitive ELISA: This assay has the advantage of simplicity. In this assay, the binding of standard diphtheria antitoxin to highly purified wild-type DT coated on ELISA plates can be inhibited by pre-incubation of the antibody (at a dilution giving 80–90% of maximal OD) with serial dilutions of wild-type toxin or formalized DT (controls) or with a mutant polypeptide of the invention. Two useful endpoints are 1) the concentration of wild-type toxin or mutant polypeptide required to inhibit binding of 50% of the antibody and 2) the maximum inhibition achieved with the polypeptides of the invention. The former provides a measure of the relative antigenicity of a polypeptide of the invention and wild-type toxin. The latter demonstrates whether all epitopes are preserved on the polypeptide. If antibodies to epitopes are not bound, the ELISA curve plateaus above the background level reached with control diphtheria toxin.

8. Evaluation of Immunogenicity A polypeptide of the invention can be tested for immunogenecity by immunizing mice and guinea pigs. Mice are more convenient and cheaper to use, and reagents for class and subclass specific antibody assays are readily available. Assays for murine antibodies have been established and standardized (see Harlow and Lane, supra). A disadvantage of mice is that they are not susceptible to diphtheria toxin because they do not have wild-type DT-binding receptors on their cells. If clearance of toxin by these receptors is responsible for the poor immunogenicity of polypeptides with intact receptor binding function, then one would not detect this problem by immunizing mice. In this case immunize guinea pigs, which are highly susceptible to diphtheria toxin, can be used. In addition, guinea pigs are the test animal for measuring the potency of diphtheria vaccine according to the U.S. Code of Federal Regulations.

(i) Screening for Immunogenicity Polypeptides of the invention will be screened for immunogenicity by giving a high dose of antigen adsorbed to aluminum phosphate to mice and guinea pigs, and measuring antibody responses at 4 weeks in both animals and also at 6 weeks in guinea pigs.

(ii) Immunization of Mice The immunizing dose for mice will be 25 $\mu$g mutant polypeptide/mouse subcutaneously given to groups of 5 mice. Controls will receive 1 $\mu$g formalinized diphtheria toxoid adsorbed on $AlPO_4$ licensed for use in pediatric vaccine. This dose produces high titers on IgG and neutralizing antibodies in mice. Four weeks after immunization, IgG anti-DT antibody will be measured by ELISA using wild-type diphtheria toxin and a polypeptide of the invention used for immunization. A pool of sera from each group of 5 mice will also be evaluated for antitoxin activity by Vero cell cytotoxicity assay (supra).

(iii) Immunization of Guinea Pigs The immunizing dose for guinea pigs will be 100 $\mu$g/animal subcutaneously given to groups of 5 animals. Controls will receive 10 Lf (25 $\mu$g) formalinized diphtheria toxoid which represents 1.5 single childhood doses of diphtheria toxoid as specified in the official U.S. potency test. Polyclonal IgG antibody concentrations in individual animals and antitoxin activity by Vero cell cytotoxicity assay in serum pools will be measured at 4 and 6 weeks. If no antibody responses are observed to a construct, one can, as appropriate, treat the construct with formalin in the presence of 0.01M lysine as described by Relyveld (supra) and reevaluate immunogenicity.

Constructs showing immunogenicity by one or more of these assays will be evaluated further for dose response and binding specificity of the antibodies induced, as described below.

(iv) Quantitative Evaluation of Immunogenicity of Diphtheria Toxin Constructs Groups of 5–10 mice will be immunized with doses of polypeptides of the invention ranging over a 100-fold dose range 0.04, 0.2, 1.0, 5.0 and 25 $\mu$g. Typically, the antigen will be adsorbed to a constant amount of aluminum phosphate, but in some instances one can also evaluate the response to soluble antigen. A booster will be given at 4 weeks, when a peak response to the primary dose has occurred and serum can be evaluated according to the following scheme.

| WEEK: | 0 | 4 | 6 |
|---|---|---|---|
| Immunization | X | X | |
| Serum for IgG ELI | | X | X |
| Pooled serum for an | | X | X |

Control mice can receive similar doses of formalinized DT toxoid. The immunogenicity of polypeptides of the invention relative to wild-type diphtheria toxoid will be compared for both total IgG antibody and neutralizing activity.

(v) Diphtheria Toxoid Potency Test in Guinea Pigs For polypeptides of the invention that are sufficiently immunogenic to be considered potential candidates for investigation in humans, we will evaluate immunogenicity in guinea pigs according to the official U.S. CFR potency test. The antitoxin induced will be evaluated in vivo to determine whether the minimum required titer of 2 Antitoxin units (AU) has been reached. Endpoint antitoxin titration will be done by the Vero cell cytotoxicity assay (supra).

(vi) Evaluation of Diphtheria Mutant Polypeptides with Terminal Hexa-Histidines PET-15b DNA vectors (Novagen) that encode polypeptides of the invention which are effective in inducing high levels of neutralizing antibody and containing an N-terminal hexa-histidine moiety will be evaluated to determine whether they induce specific antibody to the hexa-histidine peptide. Antigens with a longer 12 amino acid N-terminal tag including hexa-histidine have shown to induce small amounts of antibody. This issue can be evaluated by using as targets in ELISA non-diphtheria proteins with N-terminal hexa-histidines and hexa-histidine peptides coupled to plastic with or without a spacer peptide.

(vii) Evaluation of Diphtheria Toxin Polypeptides as Carrier Proteins for Conjugates Using the chemical coupling procedures described below, polysaccharides from *H. influenzae* b or one of the common pneumoccal types (type 14, 6B or 23F) will be covalently linked to polypeptides of the invention comprising one or more cysteines.

9. Preparation and Use of a Polypeptide Vaccine

A polypeptide toxoid of the invention can be expressed in any known protein expression system and then purified by standard means (see above methods).

A purified polypeptide of the invention may be combined with a physiologically acceptable carrier (such as physiological saline); with an adjuvant that increases immunogenicity (such as aluminum salts, bacterial endotoxins or attenuated bacterial strains (e.g., BCG or *Bordetella pertussis*, attenuated viruses, liposomes, microspheres, or Freund's complete or incomplete adjuvant); and/or with additional toxoids or killed or other vaccine strains (to form a multivalent vaccine). Such a vaccine may then be administered to a human subject by any acceptable method, including but not limited to oral, parenteral, transdermal and transmucosal delivery. Administration can be in a sustained release formulation using a biodegradable biocompatible polymer, such as a microsphere, by on-site delivery using micelles, gels or liposomes, or by transgenic modes (e.g., by biolistic administration of the DNA of the invention directly into the patient's cells, as described by Tang et al., *Nature* 356:152–154, 1992, herein incorporated by reference).

10. Preparation and Use of Live Recombinant Vaccines

Appropriate live carrier organisms include attenuated microorganisms such as BCG, Salmonella sp., *E. coli*, *Vibrio cholerae*, Streptococci, Listeriae, and Yersiniae. The DNA of the invention can be stably transfected into such a microbial strain by standard methods (Sambrook et al., *Molecular Cloning: A Laboratory Manual*. Cold Spring Harbor Lab. Press, New York, 1989.), and introduced into a patient by, for example, oral or parenteral administration. Once introduced into the patient, the bacterium would multiply and express a mutant form of diphtheria toxin within the patient, causing the patient to maintain a protective level of antibodies to the mutant toxin. In a similar manner, an attenuated animal virus such as adenovirus, herpes virus, vaccinia virus, polio, fowl pox, or even attenuated eukaryotic parasites such as Leishmania may be employed as the carrier organism. A DNA of the invention comprising a mutant R domain can be incorporated by genetic engineering techniques into the genome of any appropriate virus, which is then introduced into a human vaccinee by standard methods. A live vaccine of the invention can be administered at, for example, about $10^4$–$10^8$ organisms/dose, or a dose that is sufficient to stably induce protective levels of antitoxin. Actual dosages of such a vaccine can be readily determined by one of ordinary skill in the field of vaccine technology.

11. Preparation of Polypeptide Polysaccharide Conjugates

Conjugate proteins comprising a polypeptide may be prepared as follows:

Polysaccharides may be derivatized by adipic acid dihydrazide using CNBr to introduce hydrazide groups into the polysaccharide. The hydrazide groups are iodoacetylated with N-iodoacetyl-B-alanine-N-hydroxysuccinimide. The protein can be thiolated with N-succinimidyl-S-acetylthioacetate. The activated polysaccharide and thiolated protein can be combined to form thioether bonds between them. A detailed protocol may be found in Anderson, et al., *J. of Immunol.* 142:2464–2468 (1989). The conjugates can be evaluated for immunogenecity as described previously.

12. Administration and In Vivo Testing of a Vaccine

Polypeptides of the invention or the receptor binding domain of wild-type DT can be administered to a mammal, particularly a human, by any appropriate method: e.g., orally, parenterally, transdermally, or transmucosally. Administration can be in a sustained release formulation using a biodegradable biocompatible polymer, by on-site delivery using micelles, gels and liposomes, or by transgenic modes. Therapeutic doses can be, but are not necessarily, in the range of 0.1–10.0 mg/kg body weight, or a range that is clinically determined as appropriate by those schooled in the art.

Guinea pigs (or another species which is naturally sensitive to the cell-killing effects of diphtheria toxin) can be immunized with a toxoid of the invention according to the following protocol: between 1 and 50 $\mu$g toxoid, suspended in 50–100 $\mu$l of Freund's complete adjuvant, is subcutaneously injected into a guinea pig on day 1, day 12, and day 24. Blood samples are then assayed for antitoxin antibodies by testing serial dilutions for reactivity to naturally occurring diphtheria toxin. (See above methods.) Those animals which received high enough doses of toxoid to induce antitoxoid formation as determined by Western Blotting or ELISA can be challenged with wild-type diphtheria toxin, in order to see whether the antibodies are protective. Those toxoids of the invention which induce a positive response in the above assay are likely candidates for incorporation into live vaccines.

Appropriate live vaccine microorganisms (cells or viruses) genetically engineered to express a toxoid of the invention can be tested by injecting the candidate vaccine into an animal sensitive to wild-type DT, for example, a guinea pig, and, after a 2–3 month incubation period, challenging the animal with either a) a lethal dose of wild-type DT, or b) multiple, serially administered doses of wild-type DT, so as to calibrate the range of acquired immunity.

A polypeptide of the invention or the receptor binding domain of wild-type DT which protects against wild-type DT can be administered directly to a human patient as the immunogen in a vaccine against diphtheria toxin. Alternatively, a polypeptide of the invention or the receptor binding domain of wild-type DT can be administered in a live vaccine strain. An administered live vaccine strain can proliferate, express the cloned protective protein antigen, and confer protection from both the attenuated organism itself, wild-type DT, or from the cloned antigen, e.g., a polypeptide of the invention or the receptor binding domain of wild-type DT. Examples of live vaccine strains include, but are not limited to, BCG, Salmonella sp., and *Vibrio cholerae*. Transformation of one of these strains with DNA encoding a polypeptide of the invention can be accomplished by conventional methods known to those schooled in the art, for example, calcium phosphate precipitation or electroporation.

A vaccine can also be carried by an attenuated virus, such as adenovirus, herpes virus, or vaccinia virus. Alternatively, the vaccine can be administered by biolistic transfer, which incorporates the DNA encoding an expressible form of a polypeptide of the invention or the receptor binding domain of wild-type DT directly into cells of the vaccinee.

OTHER EMBODIMENTS

Polypeptides comprising a mutant R domain may also bear another mutation, preferably within the Diphtheria toxin catalytic region, in order to hinder catalysis and make said polypeptides safer to use. For example, a mutant form of diphtheria toxin fragment A can be generated which lacks Glu 142, Val 147 and Glu 148, or which lacks all of the residues from Glu 142 to Glu 148, inclusive. Such a mutant fragment A can be combined with a mutant R domain of the invention by using molecular techniques well known in the art. Other amino acid residues that have been shown to be essential for the biological activity of diphtheria toxin include residues His 21, Glu 22, Lys 39, Gly 52, Gly 79, Gly 128, Ala 158, and Gly 162 of the fragment A portion of diphtheria toxin, and residues Glu 349, Asp 352, and Ile 364 of the fragment B portion. Mutations in any one or more of these residues, in addition to mutations in both Val 147 and Glu 148, may be combined with the mutant R domain polypeptides of the invention by using molecular techniques well known in the art. Such mutant diphtheria toxin polypeptides comprising a mutant R domain and at least one of the additional amino acid changes in the A or B fragment described above, may be good candidates for a vaccine exhibiting little or no toxicity.

What is claimed is:

1. A substantially pure polypeptide comprising a mutant diphtheria toxin R domain, said R domain comprising a mutation in at least one or more residues from the group consisting of Lys 516, Lys 526, Phe 530, and Lys 534 of wild-type diphtheria toxin, said polypeptide binds sensitive cells with less affinity than wild-type diphtheria toxin and forms an immune complex with an antibody which specifically recognizes the R domain of wild-type diphtheria toxin.

2. The polypeptide of claim 1, in which at least one or more residues from the group consisting of Lys 516, Lys 526, and Lys 534 is replaced by either Cys or Phe.

3. The polypeptide of claim 1, in which said Phe 530 is substituted by any one of the group consisting of Glu, Lys, or Gln.

4. The polypeptide of any one of claims 1–3, said polypeptide further comprising at least part of diphtheria toxin fragment B, wherein said fragment B lacks the segment between amino acids 379–535, inclusively, of wild-type diphtheria toxin.

5. The polypeptide of any one of claims 1–3, said polypeptide comprising at least part of diphtheria toxin fragment A.

6. The polypeptide of claim 4, said polypeptide comprising at least part of diphtheria toxin fragment A.

7. The polypeptide of claim 4, said polypeptide comprising all of diphtheria toxin fragment A.

8. A vaccine comprising the polypeptide of any one of claims 1–3 and a physiologically acceptable carrier.

9. A vaccine comprising the polypeptide of claim 4 and a physiologically acceptable carrier.

10. A vaccine comprising the polypeptide of claim 5 and a physiologically acceptable carrier.

11. A live vaccine strain comprising a cell comprising DNA encoding the polypeptide of claim 1, said cell being any one of a *B. subtilis*, BCG, Salmonella sp., *Vibrio*

*cholerae*, Listeriae, Yersiniae, *Streptococci, Corynebacterium diphtheriae*, or an *E. coli* cell.

12. A live vaccine strain comprising a cell comprising DNA encoding the polypeptide of claim 4, said cell being any one of a *B. subtilis*, BCG, Salmonella sp., *Vibrio cholerae*, Listeriae, Yersiniae, Streptococci, *Corynebacterium diphtheriae*, or an *E. coli* cell.

13. A live vaccine strain comprising a cell comprising DNA encoding the RolyDeptide of claim 5, said cell being any one of a *B. subtilis*, BCG, Salmonella sp., *Vibrio cholerae*, Listeriae, Yersiniae, Streptococci, *Corynebacterium diphtheriae*, or an *E. coli* cell.

14. A method of preparing a polypeptide comprising:
   providing the cell of claim 11,
   growing said cell in a medium to form a population of cells that express said polypeptide, and
   obtaining said polypeptide from said population of cells or said medium.

15. A method of preparing a polypeptide comprising:
   providing the cell of claim 12,
   growing said cell in a medium to form a population of cells that express said polypeptide, and
   obtaining said polypeptide from said population of cells or said medium.

16. A method of preparing a polypeptide comprising:
   providing the cell of claim 13,
   growing said cell in a medium to form a population of cells that express said polypeptide, and
   obtaining said polypeptide from said population of cells or said medium.

17. A method for immunizing a mammal against wild-type diphtheria toxin, comprising introducing an immunizing amount of the vaccine of claim 8 into said mammal.

18. A method for immunizing a mammal against wild-type diphtheria toxin, comprising introducing an immunizing amount of the vaccine of claim 9 into said mammal.

19. A method for immunizing a mammal against wild-type diphtheria toxin, comprising introducing an immunizing amount of the vaccine of claim 10 into said mammal.

20. The method of claim 17, wherein said mammal is a human.

21. The method of claim 18, wherein said mammal is a human.

22. The method of claim 19, wherein said mammal is a human.

23. A fusion polypeptide comprising the polypeptide of any one of claims 1–3, linked by a peptide bond to a second polypeptide.

24. A fusion polypeptide comprising the polypeptide of claim 4 linked by a peptide bond to a second polypeptide.

25. A fusion polypeptide comprising the polypeptide of claim 5 linked by a peptide bond to a second polypeptide.

26. A substantially pure polypeptide comprising a mutant diphtheria toxin R domain, said mutant R domain having the sequence of the wild-type diphtheria toxin R-domain, in which Ala is substituted for Lys 516.

27. A substantially pure polypeptide comprising a mutant diphtheria toxin R domain, said mutant R domain having the sequence of the wild-type diphtheria toxin R-domain, in which Ala is substituted for Phe 530.

* * * * *

```
                            SEQUENCE LISTING (1) GENERAL INFORMATION:

(iii) NUMBER OF SEQUENCES:    28

(2) INFORMATION FOR SEQ ID NO:    1:

(i) SEQUENCE CHARACTERISTICS:
        (A) LENGTH:            1942
        (B) TYPE:              nucleic acid
        (C) STRANDEDNESS:      double
        (D) TOPOLOGY:          linear (xi) SEQUENCE DESCRIPTION: SEQ ID NO: 1:

CCGGCGTTGC GTATCCAGTG GCTACACTCA GGTTGTAATG ATTGGGATGA TGTACCTGAT    60

CTGAGAGCGA TTAAAAACTC ATTGAGGAGT AGGTCCCGAT TGGTTTTTGC TAGTGAAGCT   120

TAGCTAGCTT TCCCCATGTA ACCAATCTAT CAAAAAAGGG CATTGATTTC AGAGCACCCT   180

TATAATTAGG ATAGCTTTAC CTAATTATTT TATGAGTCCT GGTAAGGGGA TACGTTGTGA   240

GCAGAAAACT GTTTGCGTCA ATCTTAATAG GGGCGCTACT GGGGATAGGG GCCCCACCTT   300

CAGCCCATGC A                                                       311

GGC GCT GAT GAT GTT GTT GAT TCT TCT AAA TCT TTT GTG ATG GAA AAC    359
Gly Ala Asp Asp Val Val Asp Ser Ser Lys Ser Phe Val Met Glu Asn
1               5                   10                  15

TTT TCT TCG TAC CAC GGG ACT AAA CCT GGT TAT GTA GAT TCC ATT CAA    407
Phe Ser Ser Tyr His Gly Thr Lys Pro Gly Tyr Val Asp Ser Ile Gln
            20                  25                  30

AAA GGT ATA CAA AAG CCA AAA TCT GGT ACA CAA GGA AAT TAT GAC GAT    455
Lys Gly Ile Gln Lys Pro Lys Ser Gly Thr Gln Gly Asn Tyr Asp Asp
        35                  40                  45

GAT TGG AAA GGG TTT TAT AGT ACC GAC AAT AAA TAC GAC GCT GCG GGA    503
Asp Trp Lys Gly Phe Tyr Ser Thr Asp Asn Lys Tyr Asp Ala Ala Gly
    50                  55                  60

TAC TCT GTA GAT AAT GAA AAC CCG CTC TCT GGA AAA GCT GGA GGC GTG    551
Tyr Ser Val Asp Asn Glu Asn Pro Leu Ser Gly Lys Ala Gly Gly Val
65                  70                  75                  80

GTC AAA GTG ACG TAT CCA GGA CTG ACG AAG GTT CTC GCA CTA AAA GTG    599
Val Lys Val Thr Tyr Pro Gly Leu Thr Lys Val Leu Ala Leu Lys Val
```

```
                              85                  90                  95
GAT AAT GCC GAA ACT ATT AAG AAA GAG TTA GGT TTA AGT CTC ACT GAA    647
Asp Asn Ala Glu Thr Ile Lys Lys Glu Leu Gly Leu Ser Leu Thr Glu
            100                 105                 110

CCG TTG ATG GAG CAA GTC GGA ACG GAA GAG TTT ATC AAA AGG TTC GGT    695
Pro Leu Met Glu Gln Val Gly Thr Glu Glu Phe Ile Lys Arg Phe Gly
            115                 120                 125

GAT GGT GCT TCG CGT GTA GTG CTC AGC CTT CCC TTC GCT GAG GGG AGT    743
Asp Gly Ala Ser Arg Val Val Leu Ser Leu Pro Phe Ala Glu Gly Ser
            130                 135                 140

TCT AGC GTT GAA TAT ATT AAT AAC TGG GAA CAG GCG AAA GCG TTA AGC    791
Ser Ser Val Glu Tyr Ile Asn Asn Trp Glu Gln Ala Lys Ala Leu Ser
145                 150                 155                 160

GTA GAA CTT GAG ATT AAT TTT GAA ACC CGT GGA AAA CGT GGC CAA GAT    839
Val Glu Leu Glu Ile Asn Phe Glu Thr Arg Gly Lys Arg Gly Gln Asp
                165                 170                 175

GCG ATG TAT GAG TAT ATG GCT CAA GCC TGT GCA GGA AAT CGT GTC AGG    887
Ala Met Tyr Glu Tyr Met Ala Gln Ala Cys Ala Gly Asn Arg Val Arg
            180                 185                 190

CGA TCA GTA GGT AGC TCA TTG TCA TGC ATA AAT CTT GAT TGG GAT GTC    935
Arg Ser Val Gly Ser Ser Leu Ser Cys Ile Asn Leu Asp Trp Asp Val
            195                 200                 205

ATA AGG GAT AAA ACT AAG ACA AAG ATA GAG TCT TTG AAA GAG CAT GGC    983
Ile Arg Asp Lys Thr Lys Thr Lys Ile Glu Ser Leu Lys Glu His Gly
210                 215                 220

CCT ATC AAA AAT AAA ATG AGC GAA AGT CCC AAT AAA ACA GTA TCT GAG   1031
Pro Ile Lys Asn Lys Met Ser Glu Ser Pro Asn Lys Thr Val Ser Glu
225                 230                 235                 240

GAA AAA GCT AAA CAA TAC CTA GAA GAA TTT CAT CAA ACG GCA TTA GAG   1079
Glu Lys Ala Lys Gln Tyr Leu Glu Glu Phe His Gln Thr Ala Leu Glu
                245                 250                 255

CAT CCT GAA TTG TCA GAA CTT AAA ACC GTT ACT GGG ACC AAT CCT GTA   1127
His Pro Glu Leu Ser Glu Leu Lys Thr Val Thr Gly Thr Asn Pro Val
            260                 265                 270

TTC GCT GGG GCT AAC TAT GCG GCG TGG GCA GTA AAC GTT GCG CAA GTT   1175
Phe Ala Gly Ala Asn Tyr Ala Ala Trp Ala Val Asn Val Ala Gln Val
            275                 280                 285

ATC GAT AGC GAA ACA GCT GAT AAT TTG GAA AAG ACA ACT GCT GCT CTT   1223
Ile Asp Ser Glu Thr Ala Asp Asn Leu Glu Lys Thr Thr Ala Ala Leu
            290                 295                 300

TCG ATA CTT CCT GGT ATC GGT AGC GTA ATG GGC ATT GCA GAC GGT GCC   1271
Ser Ile Leu Pro Gly Ile Gly Ser Val Met Gly Ile Ala Asp Gly Ala
305                 310                 315                 320

GTT CAC CAC AAT ACA GAA GAG ATA GTG GCA CAA TCA ATA GCT TTA TCG   1319
Val His His Asn Thr Glu Glu Ile Val Ala Gln Ser Ile Ala Leu Ser
                325                 330                 335

TCT TTA ATG GTT GCT CAA GCT ATT CCA TTG GTA GGA GAG CTA GTT GAT   1367
Ser Leu Met Val Ala Gln Ala Ile Pro Leu Val Gly Glu Leu Val Asp
            340                 345                 350

ATT GGT TTC GCT GCA TAT AAT TTT GTA GAG AGT ATT ATC AAT TTA TTT   1415
Ile Gly Phe Ala Ala Tyr Asn Phe Val Glu Ser Ile Ile Asn Leu Phe
            355                 360                 365

CAA GTA GTT CAT AAT TCG TAT AAT CGT CCC GCG TAT TCT CCG GGG CAT   1463
Gln Val Val His Asn Ser Tyr Asn Arg Pro Ala Tyr Ser Pro Gly His
            370                 375                 380

AAA ACG CAA CCA TTT CTT CAT GAC GGG TAT GCT GTC AGT TGG AAC ACT   1511
Lys Thr Gln Pro Phe Leu His Asp Gly Tyr Ala Val Ser Trp Asn Thr
385                 390                 395                 400

GTT GAA GAT TCG ATA ATC CGA ACT GGT TTT CAA GGG GAG AGT GGG CAC   1559
Val Glu Asp Ser Ile Ile Arg Thr Gly Phe Gln Gly Glu Ser Gly His
```

```
                    405                 410                 415
GAC ATA AAA ATT ACT GCT GAA AAT ACC CCG CTT CCA ATC GCG GGT GTC    1607
Asp Ile Lys Ile Thr Ala Glu Asn Thr Pro Leu Pro Ile Ala Gly Val
            420                 425                 430

CTA CTA CCG ACT ATT CCT GGA AAG CTG GAC GTT AAT AAG TCC AAG ACT    1655
Leu Leu Pro Thr Ile Pro Gly Lys Leu Asp Val Asn Lys Ser Lys Thr
        435                 440                 445

CAT ATT TCC GTA AAT GGT CGG AAA ATA AGG ATG CGT TGC AGA GCT ATA    1703
His Ile Ser Val Asn Gly Arg Lys Ile Arg Met Arg Cys Arg Ala Ile
        450                 455                 460

GAC GGT GAT GTA ACT TTT TGT CGC CCT AAA TCT CCT GTT TAT GTT GGT    1751
Asp Gly Asp Val Thr Phe Cys Arg Pro Lys Ser Pro Val Tyr Val Gly
465                 470                 475                 480

AAT GGT GTG CAT GCG AAT CTT CAC GTG GCA TTT CAC AGA AGC AGC TCG    1799
Asn Gly Val His Ala Asn Leu His Val Ala Phe His Arg Ser Ser Ser
                485                 490                 495

GAG AAA ATT CAT TCT AAT GAA ATT TCG TCG GAT TCC ATA GGC GTT CTT    1847
Glu Lys Ile His Ser Asn Glu Ile Ser Ser Asp Ser Ile Gly Val Leu
            500                 505                 510

GGG TAC CAG AAA ACA GTA GAT CAC ACC AAG GTT AAT TCT AAG CTA TCG    1895
Gly Tyr Gln Lys Thr Val Asp His Thr Lys Val Asn Ser Lys Leu Ser
        515                 520                 525

CTA TTT TTT GAA ATC AAA AGC TGAAAGGTAG TGGGGTCGTG TGCCGG          1942
Leu Phe Phe Glu Ile Lys Ser
        530                 535

(2) INFORMATION FOR SEQ ID NO:   2:

(i) SEQUENCE CHARACTERISTICS:
        (A) LENGTH:              1942
        (B) TYPE:                nucleic acid
        (C) STRANDEDNESS:        double
        (D) TOPOLOGY:            linear (ix) FEATURE:
        (D) OTHER INFORMATION:  Xaa in location 516 is either Cys,
Phe, Glu or Ala; Xaa in location 526 is either Cys, Phe, Glu, or Ala;
Xaa in location 530 is either Glu, Lys, Gln or Ala; Xaa in location
534 is either Cys, Phe, Glu, or Ala.

(xi) SEQUENCE DESCRIPTION: SEQ ID NO: 2:

CCGGCGTTGC GTATCCAGTG GCTACACTCA GGTTGTAATG ATTGGGATGA TGTACCTGAT    60

CTGAGAGCGA TTAAAAACTC ATTGAGGAGT AGGTCCCGAT TGGTTTTTGC TAGTGAAGCT   120

TAGCTAGCTT TCCCCATGTA ACCAATCTAT CAAAAAAGGG CATTGATTTC AGAGCACCCT   180

TATAATTAGG ATAGCTTTAC CTAATTATTT TATGAGTCCT GGTAAGGGGA TACGTTGTGA   240

GCAGAAAACT GTTTGCGTCA ATCTTAATAG GGGCGCTACT GGGGATAGGG GCCCCACCTT   300

CAGCCCATGC A                                                       311

GGC GCT GAT GAT GTT GTT GAT TCT TCT AAA TCT TTT GTG ATG GAA AAC    359
Gly Ala Asp Asp Val Val Asp Ser Ser Lys Ser Phe Val Met Glu Asn
1               5                   10                  15

TTT TCT TCG TAC CAC GGG ACT AAA CCT GGT TAT GTA GAT TCC ATT CAA    407
Phe Ser Ser Tyr His Gly Thr Lys Pro Gly Tyr Val Asp Ser Ile Gln
            20                  25                  30

AAA GGT ATA CAA AAG CCA AAA TCT GGT ACA CAA GGA AAT TAT GAC GAT    455
Lys Gly Ile Gln Lys Pro Lys Ser Gly Thr Gln Gly Asn Tyr Asp Asp
        35                  40                  45

GAT TGG AAA GGG TTT TAT AGT ACC GAC AAT AAA TAC GAC GCT GCG GGA    503
Asp Trp Lys Gly Phe Tyr Ser Thr Asp Asn Lys Tyr Asp Ala Ala Gly
    50                  55                  60

TAC TCT GTA GAT AAT GAA AAC CCG CTC TCT GGA AAA GCT GGA GGC GTG    551
```

```
                Tyr Ser Val Asp Asn Glu Asn Pro Leu Ser Gly Lys Ala Gly Gly Val
                 65              70                  75                  80

GTC AAA GTG ACG TAT CCA GGA CTG ACG AAG GTT CTC GCA CTA AAA GTG              599
Val Lys Val Thr Tyr Pro Gly Leu Thr Lys Val Leu Ala Leu Lys Val
                 85                  90                  95

GAT AAT GCC GAA ACT ATT AAG AAA GAG TTA GGT TTA AGT CTC ACT GAA              647
Asp Asn Ala Glu Thr Ile Lys Lys Glu Leu Gly Leu Ser Leu Thr Glu
                100                 105                 110

CCG TTG ATG GAG CAA GTC GGA ACG GAA GAG TTT ATC AAA AGG TTC GGT              695
Pro Leu Met Glu Gln Val Gly Thr Glu Glu Phe Ile Lys Arg Phe Gly
                115                 120                 125

GAT GGT GCT TCG CGT GTA GTG CTC AGC CTT CCC TTC GCT GAG GGG AGT              743
Asp Gly Ala Ser Arg Val Val Leu Ser Leu Pro Phe Ala Glu Gly Ser
                130                 135                 140

TCT AGC GTT GAA TAT ATT AAT AAC TGG GAA CAG GCG AAA GCG TTA AGC              791
Ser Ser Val Glu Tyr Ile Asn Asn Trp Glu Gln Ala Lys Ala Leu Ser
145                 150                 155                 160

GTA GAA CTT GAG ATT AAT TTT GAA ACC CGT GGA AAA CGT GGC CAA GAT              839
Val Glu Leu Glu Ile Asn Phe Glu Thr Arg Gly Lys Arg Gly Gln Asp
                165                 170                 175

GCG ATG TAT GAG TAT ATG GCT CAA GCC TGT GCA GGA AAT CGT GTC AGG              887
Ala Met Tyr Glu Tyr Met Ala Gln Ala Cys Ala Gly Asn Arg Val Arg
                180                 185                 190

CGA TCA GTA GGT AGC TCA TTG TCA TGC ATA AAT CTT GAT TGG GAT GTC              935
Arg Ser Val Gly Ser Ser Leu Ser Cys Ile Asn Leu Asp Trp Asp Val
                195                 200                 205

ATA AGG GAT AAA ACT AAG ACA AAG ATA GAG TCT TTG AAA GAG CAT GGC              983
Ile Arg Asp Lys Thr Lys Thr Lys Ile Glu Ser Leu Lys Glu His Gly
                210                 215                 220

CCT ATC AAA AAT AAA ATG AGC GAA AGT CCC AAT AAA ACA GTA TCT GAG             1031
Pro Ile Lys Asn Lys Met Ser Glu Ser Pro Asn Lys Thr Val Ser Glu
225                 230                 235                 240

GAA AAA GCT AAA CAA TAC CTA GAA GAA TTT CAT CAA ACG GCA TTA GAG             1079
Glu Lys Ala Lys Gln Tyr Leu Glu Glu Phe His Gln Thr Ala Leu Glu
                245                 250                 255

CAT CCT GAA TTG TCA GAA CTT AAA ACC GTT ACT GGG ACC AAT CCT GTA             1127
His Pro Glu Leu Ser Glu Leu Lys Thr Val Thr Gly Thr Asn Pro Val
                260                 265                 270

TTC GCT GGG GCT AAC TAT GCG GCG TGG GCA GTA AAC GTT GCG CAA GTT             1175
Phe Ala Gly Ala Asn Tyr Ala Ala Trp Ala Val Asn Val Ala Gln Val
                275                 280                 285

ATC GAT AGC GAA ACA GCT GAT AAT TTG GAA AAG ACA ACT GCT GCT CTT             1223
Ile Asp Ser Glu Thr Ala Asp Asn Leu Glu Lys Thr Thr Ala Ala Leu
                290                 295                 300

TCG ATA CTT CCT GGT ATC GGT AGC GTA ATG GGC ATT GCA GAC GGT GCC             1271
Ser Ile Leu Pro Gly Ile Gly Ser Val Met Gly Ile Ala Asp Gly Ala
305                 310                 315                 320

GTT CAC CAC AAT ACA GAA GAG ATA GTG GCA CAA TCA ATA GCT TTA TCG             1319
Val His His Asn Thr Glu Glu Ile Val Ala Gln Ser Ile Ala Leu Ser
                325                 330                 335

TCT TTA ATG GTT GCT CAA GCT ATT CCA TTG GTA GGA GAG CTA GTT GAT             1367
Ser Leu Met Val Ala Gln Ala Ile Pro Leu Val Gly Glu Leu Val Asp
                340                 345                 350

ATT GGT TTC GCT GCA TAT AAT TTT GTA GAG AGT ATT ATC AAT TTA TTT             1415
Ile Gly Phe Ala Ala Tyr Asn Phe Val Glu Ser Ile Ile Asn Leu Phe
                355                 360                 365

CAA GTA GTT CAT AAT TCG TAT AAT CGT CCC GCG TAT TCT CCG GGG CAT             1463
Gln Val Val His Asn Ser Tyr Asn Arg Pro Ala Tyr Ser Pro Gly His
                370                 375                 380

AAA ACG CAA CCA TTT CTT CAT GAC GGG TAT GCT GTC AGT TGG AAC ACT             1511
```

```
Lys Thr Gln Pro Phe Leu His Asp Gly Tyr Ala Val Ser Trp Asn Thr
385                 390                 395                 400

GTT GAA GAT TCG ATA ATC CGA ACT GGT TTT CAA GGG GAG AGT GGG CAC      1559
Val Glu Asp Ser Ile Ile Arg Thr Gly Phe Gln Gly Glu Ser Gly His
                405                 410                 415

GAC ATA AAA ATT ACT GCT GAA AAT ACC CCG CTT CCA ATC GCG GGT GTC      1607
Asp Ile Lys Ile Thr Ala Glu Asn Thr Pro Leu Pro Ile Ala Gly Val
            420                 425                 430

CTA CTA CCG ACT ATT CCT GGA AAG CTG GAC GTT AAT AAG TCC AAG ACT      1655
Leu Leu Pro Thr Ile Pro Gly Lys Leu Asp Val Asn Lys Ser Lys Thr
        435                 440                 445

CAT ATT TCC GTA AAT GGT CGG AAA ATA AGG ATG CGT TGC AGA GCT ATA      1703
His Ile Ser Val Asn Gly Arg Lys Ile Arg Met Arg Cys Arg Ala Ile
    450                 455                 460

GAC GGT GAT GTA ACT TTT TGT CGC CCT AAA TCT CCT GTT TAT GTT GGT      1751
Asp Gly Asp Val Thr Phe Cys Arg Pro Lys Ser Pro Val Tyr Val Gly
465                 470                 475                 480

AAT GGT GTG CAT GCG AAT CTT CAC GTG GCA TTT CAC AGA AGC AGC TCG      1799
Asn Gly Val His Ala Asn Leu His Val Ala Phe His Arg Ser Ser Ser
                485                 490                 495

GAG AAA ATT CAT TCT AAT GAA ATT TCG TCG GAT TCC ATA GGC GTT CTT      1847
Glu Lys Ile His Ser Asn Glu Ile Ser Ser Asp Ser Ile Gly Val Leu
            500                 505                 510

GGG TAC CAG KNN ACA GTA GAT CAC ACC AAG GTT AAT TCT KNN CTA TCG      1895
Gly Tyr Gln Xaa Thr Val Asp His Thr Lys Val Asn Ser Xaa Leu Ser
        515                 520                 525

CTA VMN TTT GAA ATC KNN AGC TGAAAGGTAG TGGGGTCGTG TGCCGG             1942
Leu Xaa Phe Glu Ile Xaa Ser
    530                 535

(2) INFORMATION FOR SEQ ID NO:    3:

(i) SEQUENCE CHARACTERISTICS:
        (A) LENGTH:             25
        (B) TYPE:               nucleic acid
        (C) STRANDEDNESS:       single
        (D) TOPOLOGY:           linear (xi) SEQUENCE DESCRIPTION: SEQ ID NO: 3:

CGGATTCCAT AAGTGTTCTT GGGTA                                          25

(2) INFORMATION FOR SEQ ID NO:    4:

(i) SEQUENCE CHARACTERISTICS:
        (A) LENGTH:             25
        (B) TYPE:               nucleic acid
        (C) STRANDEDNESS:       single
        (D) TOPOLOGY:           linear (xi) SEQUENCE DESCRIPTION: SEQ ID NO: 4:

CCATAGGCGT TGAAGGGTAC CAGAA                                          25

(2) INFORMATION FOR SEQ ID NO:    5:

(i) SEQUENCE CHARACTERISTICS:
        (A) LENGTH:             25
        (B) TYPE:               nucleic acid
        (C) STRANDEDNESS:       single
        (D) TOPOLOGY:           linear (xi) SEQUENCE DESCRIPTION: SEQ ID NO: 5:

GCGTTCTTGG GGCCCAGAAA ACAGT                                          25

(2) INFORMATION FOR SEQ ID NO:    6:
```

```
        (i) SEQUENCE CHARACTERISTICS:
              (A) LENGTH:            25
              (B) TYPE:              nucleic acid
              (C) STRANDEDNESS:      single
              (D) TOPOLOGY:          linear (xi) SEQUENCE DESCRIPTION: SEQ ID NO: 6:

TTGGGTACCA GGAAACAGTA GATCA                                              25

(2) INFORMATION FOR SEQ ID NO:    7:

(i) SEQUENCE CHARACTERISTICS:
              (A) LENGTH:            25
              (B) TYPE:              nucleic acid
              (C) STRANDEDNESS:      single
              (D) TOPOLOGY:          linear (xi) SEQUENCE DESCRIPTION: SEQ ID NO: 7:

ACCAGAAAAC AGAAGATCAC ACCAA                                              25

(2) INFORMATION FOR SEQ ID NO:    8:

(i) SEQUENCE CHARACTERISTICS:
              (A) LENGTH:            25
              (B) TYPE:              nucleic acid
              (C) STRANDEDNESS:      single
              (D) TOPOLOGY:          linear (xi) SEQUENCE DESCRIPTION: SEQ ID NO: 8:

AAACAGTAGA TGACACCAAG GTTAA                                              25

(2) INFORMATION FOR SEQ ID NO:    9:

(i) SEQUENCE CHARACTERISTICS:
              (A) LENGTH:            25
              (B) TYPE:              nucleic acid
              (C) STRANDEDNESS:      single
              (D) TOPOLOGY:          linear (xi) SEQUENCE DESCRIPTION: SEQ ID NO: 9:

CAGTAGATCA CCGCAAGGTT AATTC                                              25

(2) INFORMATION FOR SEQ ID NO:    10:

(i) SEQUENCE CHARACTERISTICS:
              (A) LENGTH:            25
              (B) TYPE:              nucleic acid
              (C) STRANDEDNESS:      single
              (D) TOPOLOGY:          linear (xi) SEQUENCE DESCRIPTION: SEQ ID NO: 10:

TAGATCACAC CGAGGTTAAT TCTAA                                              25

(2) INFORMATION FOR SEQ ID NO:    11:

(i) SEQUENCE CHARACTERISTICS:
              (A) LENGTH:            25
              (B) TYPE:              nucleic acid
              (C) STRANDEDNESS:      single
              (D) TOPOLOGY:          linear (xi) SEQUENCE DESCRIPTION: SEQ ID NO: 11:

ATCACACCAA GGAAAATTCT AAGCT                                              25

(2) INFORMATION FOR SEQ ID NO:    12:

(i) SEQUENCE CHARACTERISTICS:
```

```
        (A) LENGTH:            25
        (B) TYPE:              nucleic acid
        (C) STRANDEDNESS:      single
        (D) TOPOLOGY:          linear (xi) SEQUENCE DESCRIPTION: SEQ ID NO: 12:

ACACCAAGGT TGCTTCTAAG CTATC                                            25

(2) INFORMATION FOR SEQ ID NO:   13:

(i) SEQUENCE CHARACTERISTICS:
        (A) LENGTH:            25
        (B) TYPE:              nucleic acid
        (C) STRANDEDNESS:      single
        (D) TOPOLOGY:          linear (xi) SEQUENCE DESCRIPTION: SEQ ID NO: 13:

CCAAGGTTAA TTTTAAGCTA TCGCT                                            25

(2) INFORMATION FOR SEQ ID NO:   14:

(i) SEQUENCE CHARACTERISTICS:
        (A) LENGTH:            25
        (B) TYPE:              nucleic acid
        (C) STRANDEDNESS:      single
        (D) TOPOLOGY:          linear (xi) SEQUENCE DESCRIPTION: SEQ ID NO: 14:

AGGTTAATTC TGAGCTATCG CTATT                                            25

(2) INFORMATION FOR SEQ ID NO:   15:

(i) SEQUENCE CHARACTERISTICS:
        (A) LENGTH:            25
        (B) TYPE:              nucleic acid
        (C) STRANDEDNESS:      single
        (D) TOPOLOGY:          linear (xi) SEQUENCE DESCRIPTION: SEQ ID NO: 15:

ATTCTAAGCT ATATCTATTT TTTGA                                            25

(2) INFORMATION FOR SEQ ID NO:   16:

(i) SEQUENCE CHARACTERISTICS:
        (A) LENGTH:            25
        (B) TYPE:              nucleic acid
        (C) STRANDEDNESS:      single
        (D) TOPOLOGY:          linear (xi) SEQUENCE DESCRIPTION: SEQ ID NO: 16:

AGCTATCGCT ATCTTTTGAA ATCAA                                            25

(2) INFORMATION FOR SEQ ID NO:   17:

(i) SEQUENCE CHARACTERISTICS:
        (A) LENGTH:            25
        (B) TYPE:              nucleic acid
        (C) STRANDEDNESS:      single
        (D) TOPOLOGY:          linear (xi) SEQUENCE DESCRIPTION: SEQ ID NO: 17:

GCGTTCTTGG GGCCCAGAAA ACAGT                                            25

(2) INFORMATION FOR SEQ ID NO:   18:

(i) SEQUENCE CHARACTERISTICS:
        (A) LENGTH:            25
        (B) TYPE:              nucleic acid
```

```
            (C) STRANDEDNESS:        single
            (D) TOPOLOGY:            linear (xi) SEQUENCE DESCRIPTION: SEQ ID NO: 18:

TTGGGTACCA GGCAACAGTA GATCA                                          25

(2) INFORMATION FOR SEQ ID NO:   19:

(i) SEQUENCE CHARACTERISTICS:
            (A) LENGTH:             25
            (B) TYPE:               nucleic acid
            (C) STRANDEDNESS:       single
            (D) TOPOLOGY:           linear (xi) SEQUENCE DESCRIPTION: SEQ ID NO: 19:

ACCAGAAAAC AGCAGATCAC ACCAA                                          25

(2) INFORMATION FOR SEQ ID NO:   20:

(i) SEQUENCE CHARACTERISTICS:
            (A) LENGTH:             25
            (B) TYPE:               nucleic acid
            (C) STRANDEDNESS:       single
            (D) TOPOLOGY:           linear (xi) SEQUENCE DESCRIPTION: SEQ ID NO: 20:

AAACAGTAGA TGCCACCAAG GTTAA                                          25

(2) INFORMATION FOR SEQ ID NO:   21:

(i) SEQUENCE CHARACTERISTICS:
            (A) LENGTH:             25
            (B) TYPE:               nucleic acid
            (C) STRANDEDNESS:       single
            (D) TOPOLOGY:           linear (xi) SEQUENCE DESCRIPTION: SEQ ID NO: 21:

CAGTAGATCA CGCCAAGGTT AATTC                                          25

(2) INFORMATION FOR SEQ ID NO:   22:

(i) SEQUENCE CHARACTERISTICS:
            (A) LENGTH:             25
            (B) TYPE:               nucleic acid
            (C) STRANDEDNESS:       single
            (D) TOPOLOGY:           linear (xi) SEQUENCE DESCRIPTION: SEQ ID NO: 22:

TAGATCACAC CGCGGTTAAT TCTAA                                          25

(2) INFORMATION FOR SEQ ID NO:   23:

(i) SEQUENCE CHARACTERISTICS:
            (A) LENGTH:             25
            (B) TYPE:               nucleic acid
            (C) STRANDEDNESS:       single
            (D) TOPOLOGY:           linear (xi) SEQUENCE DESCRIPTION: SEQ ID NO: 23:

ATCACACCAA GGCTAATTCT AAGCT                                          25

(2) INFORMATION FOR SEQ ID NO:   24:

(i) SEQUENCE CHARACTERISTICS:
            (A) LENGTH:             25
            (B) TYPE:               nucleic acid
            (C) STRANDEDNESS:       single
            (D) TOPOLOGY:           linear
```

```
       (xi) SEQUENCE DESCRIPTION: SEQ ID NO: 24:

ACACCAAGGT TGCTTCTAAG CTATC                                                 25

(2) INFORMATION FOR SEQ ID NO:    25:

(i) SEQUENCE CHARACTERISTICS:
           (A) LENGTH:           25
           (B) TYPE:             nucleic acid
           (C) STRANDEDNESS:     single
           (D) TOPOLOGY:         linear (xi) SEQUENCE DESCRIPTION: SEQ ID NO: 25:

CCAAGGTTAA TGCTAAGCTA TCGCT                                                 25

(2) INFORMATION FOR SEQ ID NO:    26:

(i) SEQUENCE CHARACTERISTICS:
           (A) LENGTH:           25
           (B) TYPE:             nucleic acid
           (C) STRANDEDNESS:     single
           (D) TOPOLOGY:         linear (xi) SEQUENCE DESCRIPTION: SEQ ID NO: 26:

AGGTTAATTC TGCGCTATCG CTATT                                                 25

(2) INFORMATION FOR SEQ ID NO:    27:

(i) SEQUENCE CHARACTERISTICS:
           (A) LENGTH:           25
           (B) TYPE:             nucleic acid
           (C) STRANDEDNESS:     single
           (D) TOPOLOGY:         linear (xi) SEQUENCE DESCRIPTION: SEQ ID NO: 27:

ATTCTAAGCT AGCGCTATTT TTTGA                                                 25

(2) INFORMATION FOR SEQ ID NO:    28:

(i) SEQUENCE CHARACTERISTICS:
           (A) LENGTH:           25
           (B) TYPE:             nucleic acid
           (C) STRANDEDNESS:     single
           (D) TOPOLOGY:         linear (xi) SEQUENCE DESCRIPTION: SEQ ID NO: 28:

AGCTATCGCT AGCTTTTGAA ATCAA                                                 25
```